(12) United States Patent
Cummins et al.

(10) Patent No.: US 9,918,859 B2
(45) Date of Patent: Mar. 20, 2018

(54) TERMINATION ASSEMBLY FOR VASCULAR INTERVENTION DEVICE DELIVERY SYSTEM

(71) Applicant: Cook Medical Technologies LLC, Bloomington, IN (US)

(72) Inventors: Sean Cummins, Limerick (IE); Darach McGrath, Tipperary (IE)

(73) Assignee: Cook Medical Technologies LLC, Bloomington, IN (US)

(*) Notice: Subject to any disclaimer, the term of this patent is extended or adjusted under 35 U.S.C. 154(b) by 174 days.

(21) Appl. No.: 14/832,247

(22) Filed: Aug. 21, 2015

(65) Prior Publication Data

US 2016/0074193 A1 Mar. 17, 2016

Related U.S. Application Data

(60) Provisional application No. 62/050,388, filed on Sep. 15, 2014.

(51) Int. Cl.
| | |
|---|---|
| *A61F 2/95* | (2013.01) |
| *A61F 2/962* | (2013.01) |
| *A61F 2/844* | (2013.01) |
| *A61F 2/966* | (2013.01) |
| *A61B 17/00* | (2006.01) |

(52) U.S. Cl.
CPC ............... *A61F 2/95* (2013.01); *A61F 2/844* (2013.01); *A61F 2/962* (2013.01); *A61F 2/966* (2013.01); *A61B 2017/00407* (2013.01); *A61F 2002/9517* (2013.01); *A61F 2230/0069* (2013.01)

(58) Field of Classification Search
CPC ............. A61F 2002/9517; A61F 2/962; A61F 2/95–2/97; A61F 2/01; A61F 2/013; A61F 2002/30713; A61B 2017/00407; A61B 90/92; A61M 25/0133; A61M 25/0147
See application file for complete search history.

(56) References Cited

U.S. PATENT DOCUMENTS

| | | |
|---|---|---|
| 6,190,360 B1 | 2/2001 | Iancea et al. |
| 6,238,402 B1 | 5/2001 | Sullivan, III et al. |
| 7,967,829 B2 | 6/2011 | Gunderson et al. |
| 7,976,574 B2 | 7/2011 | Papp |

(Continued)

FOREIGN PATENT DOCUMENTS

| | | |
|---|---|---|
| EP | 2431009 | 3/2012 |
| WO | 2008034793 | 3/2008 |

*Primary Examiner* — Eric Rosen
*Assistant Examiner* — Brooke Labranche
(74) *Attorney, Agent, or Firm* — Leill & McNeil (57) ABSTRACT

A vascular intervention device delivery system includes a thumbwheel rotatably mounted in a handle. A termination assembly is mechanically connected to the handle. A catheter extends through the termination assembly and has a proximal end attached to the handle, and a distal carrier segment for mounting a vascular intervention device. A retractable sheath is movable from a first position covering the distal carrier segment to a second position refracted proximally to uncover the distal carrier segment. A pull extends between the thumbwheel and the retractable sheath, and through the termination assembly. A stability sheath that receives the pull and the inner catheter has a proximal end that terminates in the termination assembly.

20 Claims, 4 Drawing Sheets (56) References Cited

U.S. PATENT DOCUMENTS

| | | |
|---|---|---|
| 8,500,789 B2 | 8/2013 | Wuebbeling et al. |
| 2005/0149159 A1 | 7/2005 | Andreas et al. |
| 2005/0273151 A1 | 12/2005 | Fulkerson et al. |
| 2006/0259124 A1 | 11/2006 | Matsuoka et al. |
| 2007/0032860 A1 | 2/2007 | Brooks et al. |
| 2007/0055342 A1 | 3/2007 | Wu et al. |
| 2007/0088421 A1 | 4/2007 | Loewen |
| 2007/0156225 A1 | 7/2007 | George et al. |
| 2007/0168014 A1 | 7/2007 | Jimenez et al. |
| 2008/0091257 A1 | 4/2008 | Andreas et al. |
| 2009/0210046 A1 | 8/2009 | Shumer et al. |
| 2010/0004606 A1 | 1/2010 | Hansen et al. |
| 2012/0041537 A1* | 2/2012 | Parker et al. ............ A61F 2/84 623/1.11 |
| 2012/0059448 A1 | 3/2012 | Parker et al. |
| 2012/0101562 A1 | 4/2012 | Gunderson et al. |
| 2012/0123516 A1 | 5/2012 | Gerdts et al. |
| 2012/0158120 A1 | 6/2012 | Hacker et al. |
| 2012/0330401 A1 | 12/2012 | Sugimoto et al. |
| 2013/0013047 A1 | 1/2013 | Ramos et al. |
| 2013/0018451 A1 | 1/2013 | Grabowski et al. |
| 2013/0110223 A1 | 5/2013 | Munsinger et al. |
| 2013/0211417 A1* | 8/2013 | Oboh et al. ............ A61B 17/44 606/124 |
| 2014/0188209 A1 | 7/2014 | Loewen |
| 2014/0358156 A1* | 10/2014 | Argentine ............... A61F 2/966 606/108 |
| 2015/0297378 A1* | 10/2015 | Senness et al. .......... A61F 2/95 623/1.11 |

\* cited by examiner

TERMINATION ASSEMBLY FOR VASCULAR INTERVENTION DEVICE DELIVERY SYSTEM

TECHNICAL FIELD

The present disclosure relates generally to vascular intervention device delivery systems, and more particularly to a termination assembly that receives the inner catheter(s), sheath and pull in a handle of the device.

BACKGROUND

Self expanding stents and similar vascular intervention devices are often delivered and deployed using so called pin and pull systems. Typically, the stent is compressed between a retractable outer sheath and an inner catheter. To deploy the stent, the user has to pull the outer sheath to uncover the stent using one hand while resisting the force with the other hand on the inner catheter to maintain the position of the stent during deployment. In pin and pull systems, the user can have difficulty maintaining the inner catheter at a fixed position while simultaneously moving the outer sheath. In very difficult stent deployments, which require a large amount of force by the user, this simultaneous push and pull may lead to inaccurate stent positioning, shortening or lengthening of the stent, or possibly even damage to the stent or target vessel. Another disadvantage of pin and pull systems is that there can be a lack of control on the deployment because the force to deploy the stent decreases as more of the stent is deployed. If the user maintains the same high force during deployment, the stent may be deployed too fast for the user to control. Another potential problem relates to building up tension in the outer sheath prior to movements thereof during the deployment process. If the user pauses during the deployment and releases this built up tension, deployment errors can occur when the user resumes tension to again move the outer sheath to the deployment position fully uncovering the self explaining stent. Still another problem relates to assembling the various inner catheter(s), sheaths, pull and other components in a manner that is suitable to consistent mass production and yields consistent and predictable performance.

The present disclosure is directed toward one or more of the problems set forth above.

SUMMARY OF THE DISCLOSURE

A vascular intervention device delivery system includes a thumbwheel with a radially outward thumb surface rotatably mounted in a handle. A termination assembly is also mounted in the handle. A catheter extends through the termination assembly and has a proximal end attached to the handle, and a distal carrier segment for mounting a vascular intervention device thereon. A retractable sheath is movable from a first position covering the distal carrier segment to a second position retracted proximally uncovering the distal carrier segment. A pull extends between the thumbwheel and the retractable sheath, and through the termination assembly. A stability sheath receives the pull and the catheter, and has a proximal end that terminates in the termination assembly.

DETAILED DESCRIPTION

Figure 1:
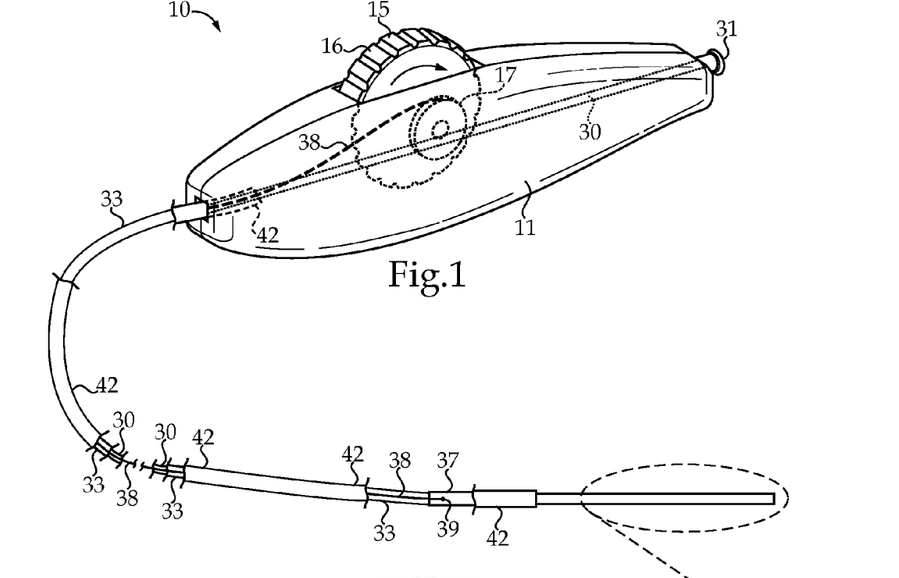
FIG. 1 is a perspective schematic view of a vascular intervention device delivery system according to the present disclosure.
Figure 2:
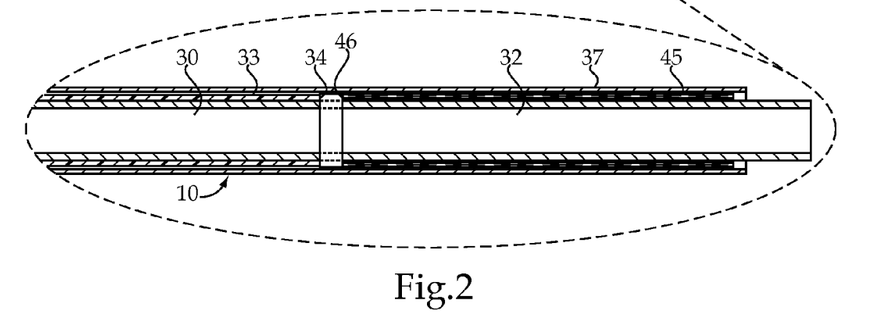
FIG. 2 is an enlarged view of the distal segment of the delivery system shown outlined with a dashed line in FIG. 1.
Figure 3:
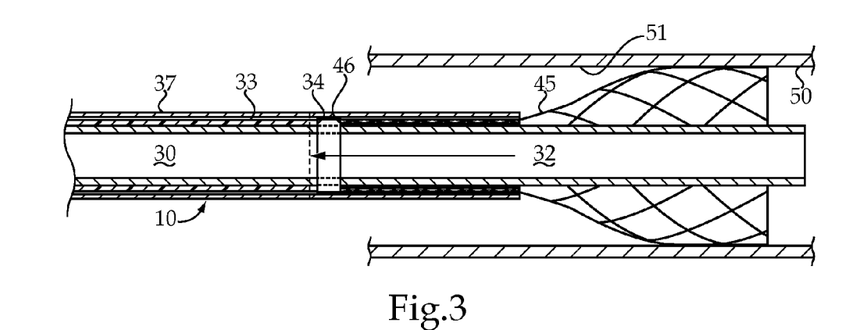
FIG. 3 is a view similar to FIG. 2 about half way through a deployment of a self expanding stent.

Referring to FIGS. 1-3, a vascular intervention device delivery system 10 is shown before and during delivery of a self expanding stent 45 into the vessel 50 of a patient. Delivery system 10 includes a handle 11 that may be gripped in one hand by a user during a delivery procedure. Handle 11 may, for instance, be manufactured from a suitable molded plastic, such as in two longitudinal halves that are joined in any suitable manner, such as via a mechanical connection, to form the complete handle 11. A thumbwheel 15 is rotatably mounted in the handle 11 and has a radially outward thumb surface 16 and a spool 17. An inner catheter 30 has a proximal end 31 attached to handle 11, and a distal carrier segment 32 for mounting a vascular intervention device, such as a self expanding stent 45, thereon. Proximal end 31 may take the form a Luer lock fitting to receive a wire guide, or so that treatment fluids or the like may be injected through inner catheter 30 in a manner well known in the art. The Luer lock fitting that comprises the proximal end 31 of inner catheter 30 may be mechanically connected to the handle, such as via an interaction between molded surfaces of the handle halves and the external surface of the Luer lock fitting. A retractable sheath 37 is movable with respect to inner catheter 30 from a first position covering the distal carrier segment 32 to a second position indicated by the dashed line in FIG. 3 at which the retractable sheath 37 has been retracted proximally to uncover the distal carrier segment 32. FIG. 3 shows the retractable sheath 37 about half way between the first position and the second position. Delivery system 10 may include an outer catheter 33 with a distal end 34 that terminates as a pusher band at a proximal end 46 of the distal carrier segment 32 in a manner similar to other stent delivery systems known in the art. The distal end 34 of outer catheter 33 may assist in preventing movement of stent 45 in a proximal direction when retractable sheath 37 is being slid from its first position toward its second position. A proximal end 35 of the outer catheter may be positioned in, and attached to, handle 11.

A pull 38 extends between the spool 17 of thumbwheel 15 and the retractable sheath 37. Pull 38, which preferably is less elastic than the retractable sheath 37, may be attached to retractable sheath 37 at an attachment 39 in any manner known in the art, such as by welding pull 38 to a metallic reinforcement of retractable sheath 37. In some versions of the vascular intervention device delivery system 10 of the present disclosure, pull 38 will be longer than retractable sheath 37. Nevertheless, retractable sheath 37 could be longer than pull 38 without departing from the present disclosure. Pull 38 may comprise a metallic wire or thin band of metal.

A wire retention/stability sheath 42 receives and surrounds a majority of the length of pull 38, and serves to keep pull 38 in close proximity to the outer surface of inner catheter 30 over much of the length of delivery system 10. Stability sheath may receive both inner catheter 30 and outer catheter 33, as shown. Wire retention/stability sheath 42 may be unattached to inner catheter 30, pull 38 or retractable sheath 37, but may be attached to handle 11 (as shown), or may be attached to move with pull 38 and/or retractable sheath 37. On the other hand, wire retention/stability sheath 42 may be attached to inner catheter 30 at one or more locations so that pull 38 and retractable sheath 37 also move with respect to wire retention/stability sheath 42 during the delivery process. In the illustrated embodiments, wire retention/stability sheath 42 terminates, and is attached at its proximal end, at a fixation point within handle 11.

When in its pre-deployment configuration, as shown in FIGS. 1 and 2, a vascular intervention device, such as a self expanding stent 45, is disposed between an outer surface of the distal carrier segment 32 of inner catheter 30, and an inner surface of the retractable sheath 37. During a typical procedure, the distal carrier segment 32 is positioned at a treatment location within a vessel 50 of a patient. After achieving proper positioning, the user then grips handle 11 and begins to rotate thumbwheel 15 so that pull 38 is wound onto spool 17. As this occurs, pull 38 and retractable sheath 37 move proximally with respect to inner catheter 30 to allow the self expanding stent 45 to expand away from carrier segment 32 and into contact with the inner wall of vessel 50 in a manner well known in the art. During this process, inner catheter 30 and outer catheter 33 may be placed in compression while both pull 38 and retractable sheath 37 are in tension. According to the present disclosure, handle 11 and thumbwheel 15 may include a structure that allows thumbwheel 16 to rotate to wind pull 38 onto spool 17, but prevent rotation in an opposite direction. This aspect of the disclosure allows the user to stop the deployment procedure while retaining the stored elastic energy in pull 38 and retractable sheath 37.

Figure 4:
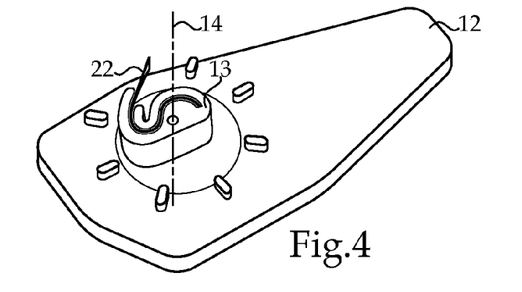
FIG. 4 is a perspective view of an assembly plate for the handle shown in FIG. 1.
Figure 5:
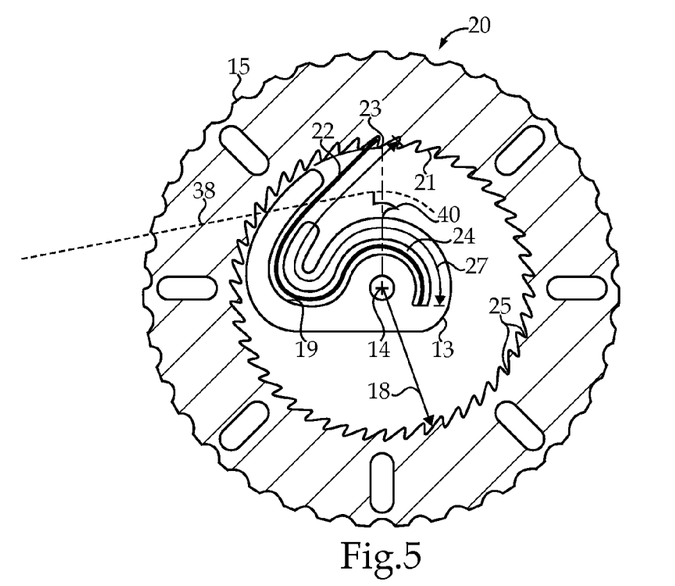
FIG. 5 is a partial sectioned view showing the ratchet according to the present disclosure.
Figure 6:
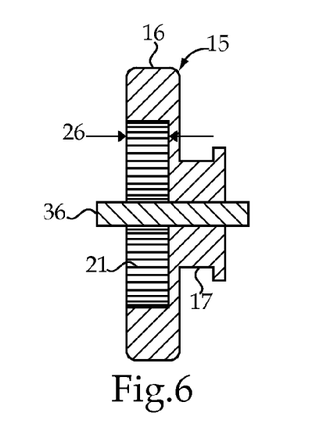
FIG. 6 is a sectioned side view through the thumbwheel of FIGS. 1 and 5.

Referring now in addition to FIGS. 4-6, a ratchet 20 provides the structure that prevents thumbwheel 16 from rotating in a forward direction. In particular, handle 11 may be formed to include, or have attached to an inner surface, an assembly plate 12 that defines a hub 13 that receives an axle 36 upon which thumbwheel 16 is rotatably mounted to rotate about axis 14 in a reverse direction permitted by ratchet 20. Thumbwheel 15 includes a radially inward ratchet surface 21 of ratchet 20. A ratchet pawl 22 of ratchet 20 is mounted in the handle 11, and has a catch 23 in contact with ratchet surface 21 of thumbwheel 15. Ratchet 20 holds thumbwheel 15 against rotation in a forward direction, but the retractable sheath 37 moves responsive to rotation of the thumbwheel 15 in a reverse direction.

In the illustrated embodiment, catch 23 takes the form of a deformed rectangular shaped band of spring steel 24 that is received in an S-shaped groove 19 defined by assembly plate 12 and oriented parallel to axis 14. The ratchet surface 21 of thumbwheel 15 may define a plurality of stops 25 in each of four 90° rotation angles. In the specific embodiment shown, ratchet surface 21 defines at least fifty stops 25 per revolution of thumbwheel 15 in order to provide the user with precise tactile control over the delivery procedure. The deformed band of spring steel 24 may have a width that contacts the ratchet surface 21 across the width 26. In addition, although not necessary, the deformed band of spring steel 24 may have a length 27 that is greater than radius 18 of thumbwheel 15. An imaginary line 40 that extends parallel from an end 28 of catch 23 to the axis 14 may be configured to be orthogonal to pull 38 where pull 38 contacts spool 37, as best shown in FIG. 5.

Referring now to FIGS. 7-14, a vascular intervention device delivery system 60 according to another aspect includes a ratchet 70 and a handle 61 with a structure that differs from that shown in relation to FIGS. 4-6. However, where similar numbers are used, those features correspond to similar features shown in FIGS. 1-3. Vascular intervention device delivery system 60 differs from the system 10 described earlier by the shape and structure of the ratchet pawl 72 and by the inclusion of a lock 80, among other features. Like the earlier version, ratchet 70 may provide a structure that prevents thumbwheel 65 from rotating in a forward direction.

Figure 7:
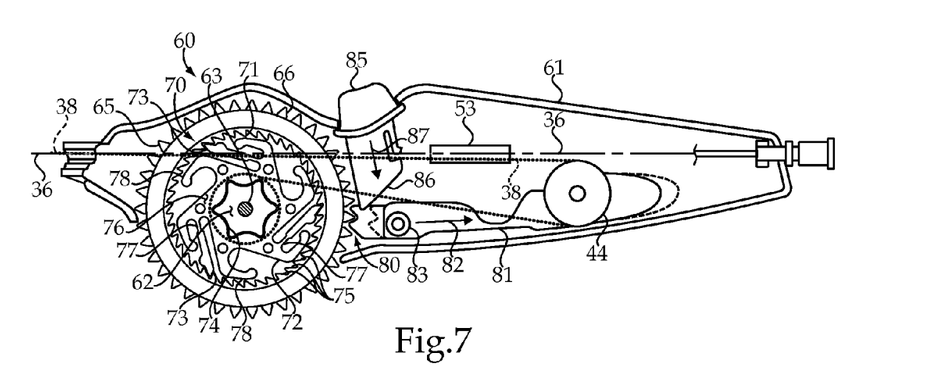
FIG. 7 is a sectioned side view of a handle portion of a vascular intervention device delivery system according to another aspect of the present disclosure.
Figure 8:
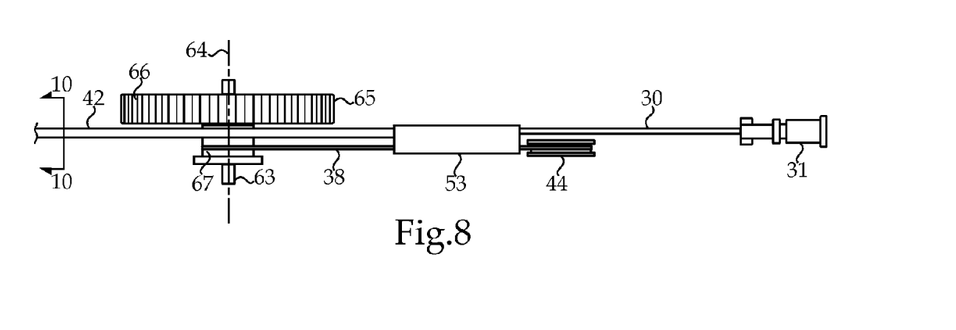
FIG. 8 is a top view of the inner workings of the vascular intervention device delivery system of FIG. 7, minus the handle.

Handle 61 may be formed from a suitable plastic to include a key shaped hub 62 that is received in a matching key shaped opening 74 defined by ratchet pawl 72. This configuration permits assembly of ratchet pawl 72 to key shaped hub 62 in a plurality of different but equivalent angular orientations. Key shaped hub 62 may define a central opening that receives an axle 63 to define an axis 64 about which thumbwheel 65 rotates. Thumbwheel 65 includes a radially outward thumb surface 66 and a radially inward ratchet surface 71. Thumbwheel 65 may also include a spool 67 upon which the pull 38 is wound when the device delivery system 60 is operated. In this version, the wire retention/stability sheath 42 terminates at a termination assembly 53 positioned within handle 61. As in the previous version, the pull 38 is positioned within the wire retention/stability sheath 42 and emerges from the termination assembly 53 to wrap around an idler wheel 44 and return in the reverse direction for being wound onto spool 67 as best shown in FIGS. 7 and 8. Termination assembly 53 may be positioned between idler wheel 44 and thumbwheel 65 along axis 36 defined by inner catheter 30. As in the previous embodiment, ratchet 70, if included, prevents thumbwheel 65 from rotating in a forward direction, but the retractable sheath 37 (FIGS. 1-3) moves responsive to rotation of thumbwheel 65 in a reverse direction.

Figure 9:
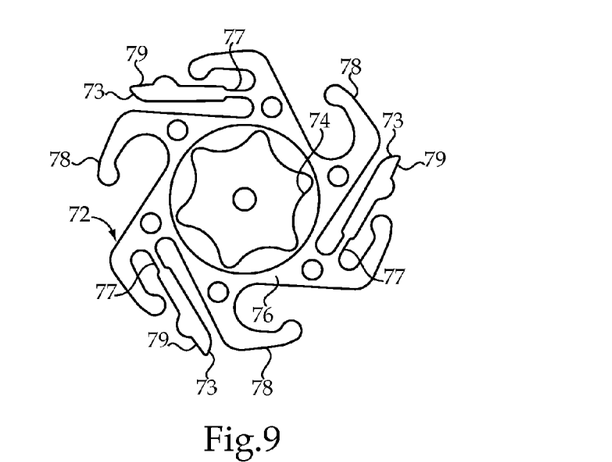
FIG. 9 is a side view of a ratchet pawl for the vascular intervention device delivery system of FIG. 7.

In this embodiment, catch 73 takes the form of spiral arms 79 that are attached to a central body 76 by living hinges 77. Unlike the ratchet pawl 22 shown in the embodiment in FIGS. 4-6, ratchet pawl 72 may most conveniently be formed of a suitable plastic material. When thumbwheel 65 is rotated in a reverse direction, each of the three catches 73 will click and be received into respective stops 75 that define ratchet surface 71. In this embodiment, ratchet catches 73 are equally distributed 120° apart around the axis 64 defined by axle 63. Thus, the three catches 73 will simultaneously contact the ratchet surface 71 at three different locations located 120° apart about axis 64. Those skilled in the art will appreciate that a ratchet pawl 72 having two, four or more catches 73 would also fall within the intended scope of this disclosure.

As best shown in FIGS. 7 and 9, the ratchet pawl 72 includes curved arms 78 that are distributed to provide a circular guide for the thumbwheel as the ratchet teeth rotate around the fixed ratchet. Thus, in some embodiments, the use of curved arms 78 could permit omission of axle 63 as shown, since the thumbwheel would rotate about axis 64 with the curved arms 78 contacting ratchet surface 71, even without the inclusion of axle 63. It is also worth noting that this embodiment differs from the earlier embodiment in that both the ratchet pawl 72 and the ratchet surface 71 of thumbwheel 65 may be made out of plastic, as opposed to a metal ratchet pawl 22 acting on a plastic ratchet surface 21 as in the earlier embodiment. By making both the pawl and the ratchet surface from the same material, the potential creation of the debris caused by the interaction of metal with plastic can be avoided.

In addition to ratchet 70, vascular intervention device delivery system 60 may include a lock 80 that allows thumbwheel 65 to be disabled during shipment and during positioning of the distal carrier segment 32 (FIGS. 1-3) at a treatment location within a patient. The lock 80 is movable between a locked position, as shown, and an unlocked position shown by dashed lines. The lock 80 includes a latch 81 positioned in handle 61 and movable along a line 82 between the locked position at which the latch 81 engages the radially outward thumb surface 66 of thumbwheel 65, and the unlocked position at which the latch 81 is out of contact with the radially outward thumb surface 66. Lock 80 also includes a pusher 85 that is at least partially positioned outside of handle 61, but on an opposite side of handle 61 from the exposed portion of thumbwheel 65. The pusher may include a wedge 86 that engages a post 83 of latch 81. Post 83 may be oriented perpendicular to the line 82 of action of latch 81. Vascular intervention device delivery system may be enabled by depressing pusher 85 along line 87 to move latch 81 out of contact with radially outward thumb surface 66 of thumbwheel 65.

Figure 10:
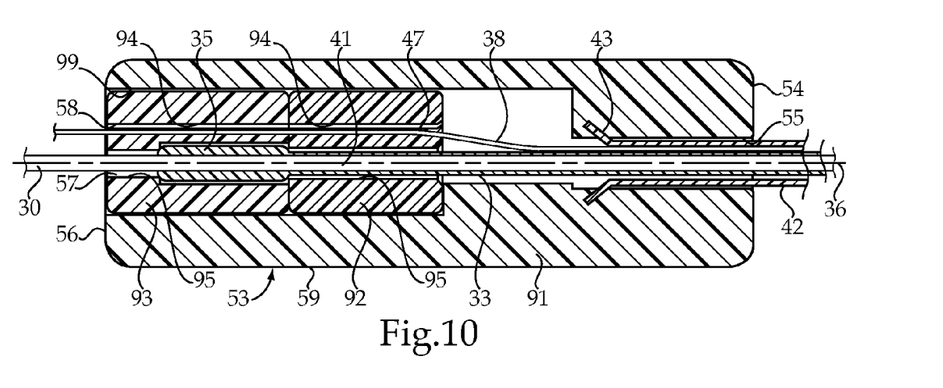
FIG. 10 is a sectioned side schematic view of the termination assembly according to one aspect of the disclosure.
Figure 11:
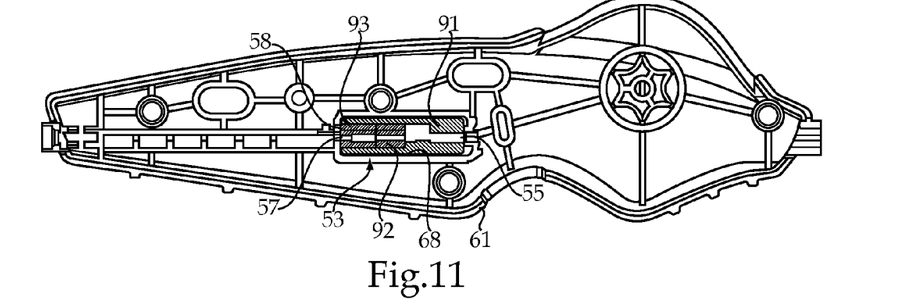
FIG. 11 is a side schematic view of a termination assembly of FIG. 10 mounted in a portion of the handle.

Referring now specifically to FIGS. 10-14, the various features of termination assembly 53 are illustrated. In particular, the termination assembly 53 is mounted in handle 61. Preferably, termination assembly 53 has an external shape 59 with a shape that matches an internal surface shape of a cage 68 defined by the handle 61. In this way, the termination assembly can be trapped in cage 68 to facilitate a mechanical connection therebetween. A proximal end 43 of stability sheath 42 terminates in termination assembly 53, preferably via a mechanical connection. In the illustrated embodiment, a flared proximal end 43 is mechanically connected to termination assembly 53 by having a first piece 91 over molded around flared proximal end 43. In the illustrated embodiment, the inner catheter 30 extends through termination assembly 53 in a straight line 41 that is also an axis 36 defined by the inner catheter 30. The outer catheter 33 has a proximal end 35 that terminates in termination assembly 53. Preferably, outer catheter 33 is mechanically connected to termination assembly 53, such as by having proximal end 35 flared and trapped within a catheter passage 95, which is defined by a third piece 93 of termination assembly 53. As best shown in FIG. 10, the pull 38 and the inner catheter 30 enter a distal end 54 of termination assembly 53 through a common distal opening 55. The inner catheter 30 and the pull 38 exit at a proximal end 56 of the termination assembly 53 through a first proximal opening 57 and a second proximal opening 58, respectively.

Figure 12:
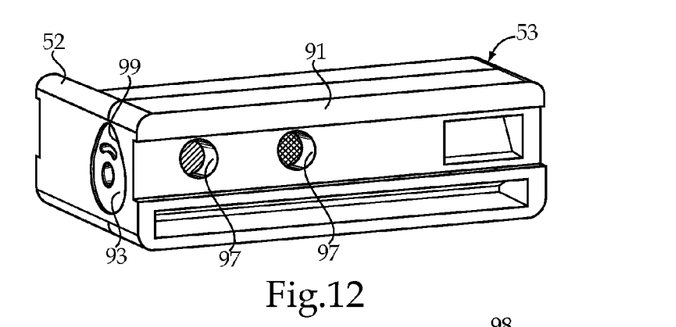
FIG. 12 is a perspective view of a first piece of the termination assembly of FIG. 10.
Figure 13:
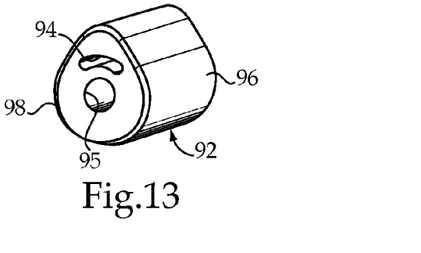
FIG. 13 is a perspective view of a second piece of the termination assembly of FIG. 10.
Figure 14:
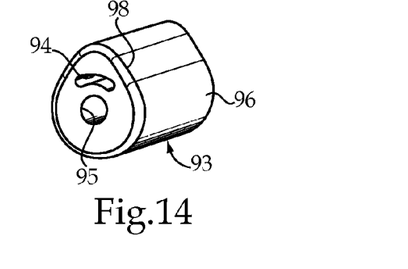
FIG. 14 is a perspective view of a third piece of the termination assembly of FIG. 10.

The termination assembly 53 may comprise a first piece 91 that is over molded around a flared proximal end 43 of the stability sheath 42. A second piece 92 is slidably received in a cavity 99 defined by the first piece 91. A third piece 93 slidably received in the cavity 99 and abuts the second piece 92. Each of the second piece 92 and the third piece 93 define a wire passage 94 that receives pull 38 therethrough. Also, each of the second piece 92 and third piece 93 also define a separate catheter passage 95 that receives inner catheter 30 therethrough. The second piece 92 and the third piece 93 may have outer surfaces 96 of contrasting colors that are visible through respective windows 97 defined by the first piece 91 in order to better prevent misassembly. For instance, second piece 92 may be formed from a red plastic, whereas third piece 93 may be formed from a white plastic. In the illustrated embodiment, each of the second piece 92 and the third piece 93 have a cross section with an identical perimeter shape 98 that matches the teardrop shape cross section of cavity 99. This feature may help prevent second piece 92 and third piece 93 from rotating within first piece 91, which has its orientation held by the interaction with the cage 68 defined by the handle 61. The termination assembly 53 helps to facilitate rerouting of pull 38 toward idler wheel 44 by following an unstraight line 47 through termination assembly 53, as best shown in FIG. 10. As best shown in FIG. 12, the termination assembly 53 may have surface features that prevent improper installation into handle 65. In particular, first piece 91 may be formed to include exactly one tab 52 extending from the termination assembly 53 and being sized to be received in the cage 68 of handle 65 in exactly one orientation.

The termination assembly 53 may facilitate a variety of mechanical connections to better facilitate consistent assembly when the vascular intervention device delivery system 10, 60 is mass produced. As used in the present disclosure, the terms mechanically connected and mechanical connection mean the joining of two or more elements without adhesives or welds. Thus, in the illustrated embodiment, both the stability sheath 42 and the outer catheter 33 are mechanically connected to the termination assembly 53, which itself is mechanically connected to handle 61. As discussed earlier, the inner catheter 30 is mechanically connected to handle 61. Preferably, the various features that make up the delivery system 60 are mechanically connected via appropriate shapes without the use of fasteners.

INDUSTRIAL APPLICABILITY

The present disclosure is generally applicable to vascular intervention device delivery systems, and more particularly to a delivery system for delivery of self expanding stents and other vascular intervention devices with self expanding action. The present disclosure finds specific applicability to delivery of relatively long vascular intervention devices that produce substantial friction on the inner surface of retractable sheath 37, and thus require higher forces on retractable sheath 37 and pull 38 in order to successfully deliver the vascular intervention device to an intended treatment site. The present disclosure is further applicable to vascular intervention device delivery system structures that may be mass produced consistently via joining of various parts via mechanical connections.

The vascular intervention device delivery system 10, 60 will typically be packaged in a conventional sterile packaging in a known manner for shipment. After a wire guide (not shown) has been positioned in a patient's body across a treatment location, the inner catheter 30 may be slid over the wire guide to position the distal carrier segment 32 and the attached self expanding stent 45 at the treatment location within the vessel 50 of the patient. Thereafter, the wire guide may be withdrawn or left in place. During this portion of the procedure, the thumbwheel 65 of the vascular intervention device delivery system 60 may be disabled by maintaining the lock 80 in its locked position as shown in FIG. 7. After the distal carrier segment 32 is properly positioned and it is now time to deploy the self expanding stent 45, the user may depress pusher 85 to disengage lock 80 and move latch 81 out of contact with the radially outward thumb surface 66 of thumbwheel 65.

A method of operating vascular intervention device delivery system 10, 60 includes rotating the thumbwheel 15, 65 in a reverse direction to wind pull 38 onto spool 17, 67 to build up tension in the retractable sheath 37 and pull 38 without moving the retractable sheath 37 relative to the distal carrier segment 32 of inner catheter 30. The "reverse direction" is clockwise for the embodiment of FIG. 1 and counterclockwise for the embodiment of FIG. 7. Next, a portion, which is less than all, of the distal carrier segment 32 is uncovered by continuing to rotate the thumbwheel 15, 65 in the reverse direction. At some point during the delivery procedure, the user may then pause rotation of the thumbwheel 15, 65 in the reverse direction. For instance, the user may pause in order to confirm that the vascular intervention device, such as a self expanding stent 45, is being delivered to the desired location in the vessel 50 of the patient. While the rotation of the thumbwheel 15, 65 is paused, tension in the pull 38 and the retractable sheath 37 is maintained by holding the ratchet 20, 70 and preventing rotation of the thumbwheel 15, 65 in the forward direction. Ratchet 20, 70 may be considered to be in a hold configuration when catches 23, 73 are received in one of the stops 25, 75 of the ratchet surface 21, 71. A remaining portion of the distal carrier segment 32 is then uncovered to facilitate complete deployment of the self expanding stent 45 by resuming rotation of the thumbwheel 15, 65 in the reverse direction until retractable sheath 37 arrives at its second position fully uncovering distal carrier segment 32.

An important aspect of the ratchet operated vascular intervention device delivery system 10, 60 of the present disclosure is to allow for rotation of thumbwheel 15, 65 in one direction only. This means that the pull 38 and hence the retractable sheath 37 can only be pulled proximally. If the thumbwheel 15, 65 were able to rotate in both directions, it could cause the pull 38 to slack and possibly jump out of the collection diameter of the spool 17, 67 on thumbwheel 15, 65. Also, by keeping the rotation of thumbwheel 15, 65 to one direction only, ratchet 20, 70 allows all of the energy already placed in the system 10, 60 by the user to be maintained. For example, if the user was to partially deploy a self expanding stent 45 that had a deployment force of 30 N they will have to put effort into getting the stent to partially deploy. This effort could have caused the sheath 37 to stretch slightly and also the inner catheter 30 to compress slightly. If this energy were lost when the thumbwheel 15, 65 were released, it would mean that when the deployment was resumed from that point, the user would have to rotate the thumbwheel 15, 65 an amount in order to reestablish tension in the system 10, 60 again before the self expanding stent 45 would continue to deploy. This may be especially important in the case of deploying longer stents that require higher forces.

It should be understood that the above description is intended for illustrative purposes only, and is not intended to limit the scope of the present disclosure in any way. Thus, those skilled in the art will appreciate that other aspects of the disclosure can be obtained from a study of the drawings, the disclosure and the appended claims.

What is claimed is:

1. A vascular intervention device delivery system comprising: a handle; a thumbwheel rotatably mounted in the handle and having a radially outward thumb surface; a termination assembly mounted in the handle and being blocked against movement with respect to the handle; a catheter extending through the termination assembly and having a proximal end attached to the handle, and a distal carrier segment for mounting a vascular intervention device thereon; a retractable sheath movable from a first position covering the distal carrier segment, to a second position retracted proximally uncovering the distal carrier segment; and a pull extending between the thumbwheel and the retractable sheath and through the termination assembly, and the pull moving through the termination assembly, which remains stationary with respect to the handle, responsive to rotation of the thumbwheel; and a stability sheath that receives the pull and the catheter, and the stability sheath having a proximal end that terminates in the termination assembly.

2. The vascular intervention device delivery system of claim 1 wherein the catheter is an inner catheter, wherein the delivery system further comprises: an outer catheter with a distal end that terminates at a proximal end of the distal carrier segment, and a proximal end that terminates in the termination assembly; and the stability sheath receives the outer catheter.

3. The vascular intervention device delivery system of claim 2 wherein the stability sheath and the outer catheter are mechanically connected to the termination assembly; and
    the termination assembly is mechanically connected to the handle.

4. The vascular intervention device delivery system of claim 3 wherein the inner catheter is mechanically connected to the handle.

5. The vascular intervention device delivery system of claim 1 wherein the termination assembly is joined to the handle by a mechanical connection.

6. The vascular intervention device delivery system of claim 1 wherein the termination assembly has an external surface with a shape that matches an internal surface shape of a cage defined by the handle; and
    the termination assembly is trapped in the cage.

7. The vascular intervention device delivery system of claim 1 wherein the catheter extends through the termination assembly in a straight line; and
    the pull extends through the termination assembly in an unstraight line.

8. The vascular intervention device delivery system of claim 1 wherein the termination assembly is positioned between an idler wheel and the thumbwheel along an axis defined by the catheter.

9. The vascular intervention device delivery system of claim 1 wherein the termination assembly includes exactly one tab extending from the termination assembly and being sized to be received in the handle in exactly one orientation.

10. The vascular intervention device delivery system of claim 1 wherein the thumbwheel defines a radially inward ratchet surface of a ratchet;

a ratchet pawl of the ratchet being mechanically connected to the handle and having a catch in contact with the ratchet surface.

11. The vascular intervention device delivery system of claim 10 wherein the termination assembly is joined to the handle by a mechanical connection.

12. A vascular intervention device delivery system comprising: a handle; a thumbwheel rotatably mounted in the handle and having a radially outward thumb surface; a termination assembly mounted in the handle and being blocked against movement with respect to the handle; a catheter extending through the termination assembly and having a proximal end attached to the handle, and a distal carrier segment for mounting a vascular intervention device thereon; a retractable sheath movable from a first position covering the distal carrier segment, to a second position retracted proximally uncovering the distal carrier segment; and a pull extending between the thumbwheel and the retractable sheath and through the termination assembly; a stability sheath that receives the pull and the catheter, and the stability sheath having a proximal end that terminates in the termination assembly: wherein the catheter and the pull enter a distal end of the termination assembly through a common distal opening; and the catheter and the pull exit a proximal end of the termination assembly through a first proximal opening and a second proximal opening, respectively.

13. A vascular intervention device delivery system comprising: a handle: a thumbwheel rotatably mounted in the handle and having a radially outward thumb surface; a termination assembly mounted in the handle and being blocked against movement with respect to the handle; a catheter extending through the termination assembly and having a proximal end attached to the handle and a distal carrier segment for mounting a vascular intervention device thereon: a retractable sheath movable from first position covering the distal carrier segment to a second position retracted proximally uncovering the distal carrier segment: and pull extending between the thumbwheel and the retractable sheath and through the termination assembly; a stability sheath that receives the pull and the catheter, and the stability sheath having a proximal end that terminates in the termination assembly; wherein the termination assembly includes a first piece over-molded around a flared proximal end of the stability sheath; a second piece slidably received in a cavity defined by the first piece; and a third piece slidably received in the cavity and abutting the second piece.

14. The vascular intervention device delivery system of claim 13, wherein the catheter is an inner catheter, and wherein each of the second piece and the third piece define a wire passage that receives the pull therethrough; and each of the second piece and the third piece define an inner catheter passage that receives the inner catheter therethrough.

15. The vascuiar intervention device delivery system of claim 14 wherein the inner catheter and the pull enter a distal end of the termination assembly through a common distal opening; and the inner catheter and the pull exit a proximal end of the termination assembly through a first proximal opening and a second proximal opening, respectively.

16. The vascular intervention device delivery system of claim 15, further comprising an outer catheter with a distal end that terminates at a proximal end of the distal carrier segment, and a proximal end that terminates in the termination assembly; and the stability sheath receives the outer catheter.

17. The vascular intervention device delivery system of claim 16 wherein the termination assembly is joined to the handle by a mechanical connection.

18. The vascular intervention device delivery system of claim 17 wherein the proximal end of the outer catheter is flared and trapped within the inner catheter passage of the third piece.

19. The vascular intervention device delivery system of claim 13 wherein the second piece and the third piece have outer surfaces of contrasting colors that are visible through respective windows defined by the first piece.

20. The vascular intervention device delivery system of claim 19 wherein each of the second piece and the third piece have a cross section with an identical perimeter shape.

* * * * *